(12) United States Patent
Wang et al.

(10) Patent No.: US 8,062,663 B2
(45) Date of Patent: Nov. 22, 2011

(54) METHODS AND COMPOSTIONS FOR ENHANCING TRANSDERMAL DRUG DELIVERY

(75) Inventors: Yu-Jing Wang, Taichung (TW); Yu-Chao Wang, Taipei (TW); Yi-Ting Wu, Taoyuan (TW); Lin-Ai Tai, Hsin-Chu (TW); Leu-Wei Lo, Taipei (TW); Chung-Shi Yang, Taichung (TW)

(73) Assignee: National Health Research Instittues, Miaoli County (TW)

( * ) Notice: Subject to any disclaimer, the term of this patent is extended or adjusted under 35 U.S.C. 154(b) by 292 days.

(21) Appl. No.: 12/466,011

(22) Filed: May 14, 2009

(65) Prior Publication Data

US 2009/0291133 A1 Nov. 26, 2009

Related U.S. Application Data

(60) Provisional application No. 61/055,784, filed on May 23, 2008.

(51) Int. Cl.
  *A61K 38/43*  (2006.01)
  *A61K 9/127*  (2006.01)
  *A61K 9/52*   (2006.01)
  *A61K 9/54*   (2006.01)
  *A61K 9/60*   (2006.01)
  *A61K 9/64*   (2006.01)

(52) U.S. Cl. ....... 424/450; 424/94.1; 424/457; 424/458; 424/459; 424/460

(58) Field of Classification Search .................. None
See application file for complete search history.

(56) References Cited

U.S. PATENT DOCUMENTS

2004/0037809 A1* 2/2004 Quay et al. ............... 424/85.6
2007/0009583 A1* 1/2007 Qvist ......................... 424/445

FOREIGN PATENT DOCUMENTS

CN          1957925 A  *  5/2007

OTHER PUBLICATIONS

Kuhn et al. Nanoletters, vol. 6, No. 2, 2006, pp. 306-312.*
E. Touitou., H. E. Jungingers.,N,. D. Weiner.,T. Naga., M. Mezei (1994) Liposome as Carriers for Topical and Trnasdermal Delivery Journal of Pharmaceutical Science 89(9): 1194-1203.
Y.C. Sim, Y.S. Nam, E.Shin, S.Kim, I.S. Chang, J. S. Rhee (2003) Proteolytic enzyme conjugated to SC-glucan as a enzymatic transdermal drug penetration enhancer Pharmazie 58:252-256.

* cited by examiner

*Primary Examiner* — Janet L Epps-Smith
(74) *Attorney, Agent, or Firm* — Hsiu-Ming Saunders; Intellectual Property Connections, Inc.

(57) ABSTRACT

Methods and compositions for enhancing transdermal delivery of a bioactive agent. The method contains the step of applying to a skin tissue an effective amount of a composition comprising: (a) a drug vehicle; (b) a bioactive agent encapsulated within the drug vehicle; (c) a plurality of proteolytic enzyme molecules conjugated onto the surface of the drug vehicle; and (d) a pharmaceutically acceptable carrier, for a period of time effective to deliver the bioactive agent across the skin tissue at a desired dosage.

19 Claims, 3 Drawing Sheets

METHODS AND COMPOSTIONS FOR ENHANCING TRANSDERMAL DRUG DELIVERY

REFERENCES TO RELATED APPLICATION

This application claims priority to the U.S. Provisional Application Ser. No. 61/055,784, filed May 23, 2008, herein incorporated by reference in its entirety.

FIELD OF THE INVENTION

The present invention relates generally to drug delivery, and more specifically to transdermal drug delivery.

BACKGROUND OF THE INVENTION

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days. When compared to injections, TDD eliminates the associated pain and the possibility of infection. Theoretically, the transdermal route of drug administration could be advantageous in the delivery of many therapeutic proteins because proteins are susceptible to gastrointestinal degradation and exhibit poor gastrointestinal uptake. Proteins such as interferon are cleared rapidly from the blood and need to be delivered at a sustained rate in order to maintain their blood concentration at a high value, and transdermal devices are easier to use than injections (U.S. Pat. No. 5,814,599).

In spite of these advantages, very few drugs and no proteins or peptides are currently administered transdermally for clinical applications because of the low skin permeability to drugs. This low permeability is attributed to the stratum corneum (SC), the outermost skin layer which consists of flat, dead cells filled with keratin fibers (keratinocytes) surrounded by lipid bilayer. The highly-ordered structure of the lipid bilayer confers an impermeable character to the SC (U.S. Pat. No. 5,814,599).

Transdermal drug delivery offers an advantageous alternative to oral delivery and injections. However, its applications are restricted to only a few drugs because of the extremely low skin permeability to drugs. Therefore, a heretofore unaddressed need exists in the art to address the aforementioned deficiencies and inadequacies, especially in connection with an improved method for transdermal drug delivery.

SUMMARY OF THE INVENTION

In one aspect, the invention relates to a method for enhancing delivery of a bioactive agent across skin. The method contains the step of applying an effective amount of a composition which includes: (a) a drug vehicle; (b) a bioactive agent encapsulated within the drug vehicle; (c) a plurality of proteolytic enzyme molecules conjugated onto the surface of the drug vehicle; and (d) a pharmaceutically acceptable carrier, for a period of time effective to deliver the bioactive agent across the skin at a desired dosage.

In one embodiment of the invention, the drug vehicle is a liposome.

In another embodiment of the invention, the bioactive agent includes two or more than two types of bioactive agents. Further in another embodiment of the invention, the bioactive agent contains at least one type of hydrophilic bioactive agent. Yet in another embodiment of the invention, the bioactive agent is a hormone.

In another embodiment of the invention, the proteolytic enzyme is selected from the group consisting of papain, pancreatin, ficin, bromelain, elastase, pepsin, hyaluronidase, streptokinase, streptodornase, trypsin, chymotrypsin, α-chymotrypsin, α-amylase, deoxyribonuclease, collagenase, sutilain and any combination thereof.

In another embodiment of the invention, the proteolytic enzyme is papain at a concentration of less than 93, or less than 50, 40 or 30 µg/ml.

Further in another aspect, the invention relates to a method for enhancing the delivery of a bioactive agent across a skin tissue. The method contains the step of applying an effective amount of a composition that comprises: (a) a liposome; (b) a bioactive agent encapsulated within the liposome; (c) a plurality of papain molecules conjugated onto the surface of the liposome; and (d) a pharmaceutically acceptable carrier, for a period of time effective to deliver the bioactive agent encapsulated in the liposome across the skin tissue at a desired dosage.

In another aspect, the invention relates to a composition for transdermal administration of a bioactive agent. The composition comprises: (a) a liposome; (b) a bioactive agent encapsulated within the liposome; (c) a plurality of proteolytic enzyme molecules conjugated onto the surface of the liposome; and (d) a pharmaceutically acceptable carrier, wherein the proteolytic enzyme is selected from the group consisting of papain, pancreatin, ficin, bromelain, elastase, pepsin, hyaluronidase, streptokinase, streptodornase, trypsin, chymotrypsin, α-chymotrypsin, α-atmylase, deoxyribonuclease, collagenase, sutilain and any combination thereof.

In one embodiment of the invention, the composition may further comprise a nanoparticle enclosed in the liposome, in which the bioactive agent is encapsulated within the nanoparicle within the liposome. The nanoparticle may be a poly (lactic-co-glycolic acid) (PLGA) or hydro-gel nanoparicle.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
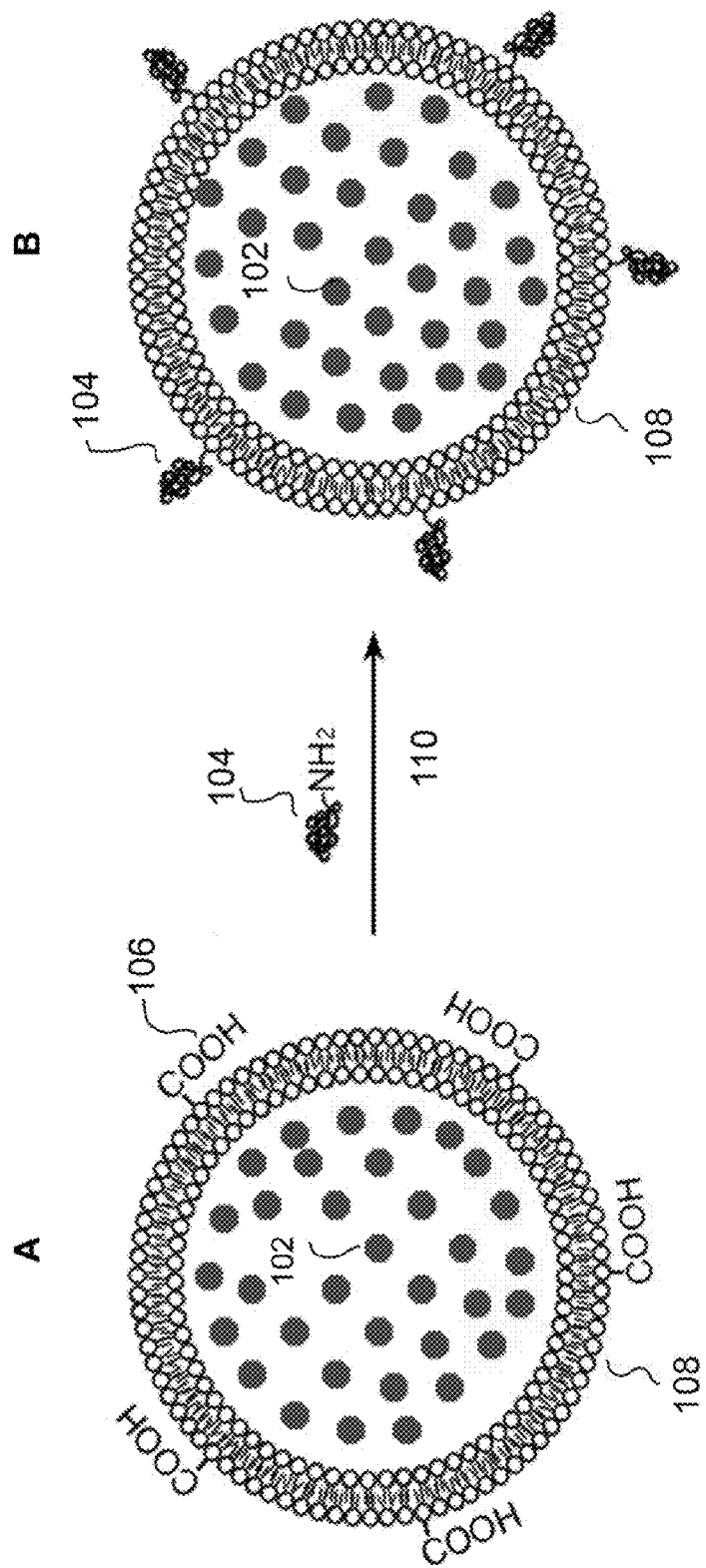
FIG. 1 is a schematic drawing showing that a bioactive molecules-encapsulated liposome (A) undergoes an EDC coupling reaction with papain (as indicated by the arrow) to form a papain-conjugated liposome (B).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Preparation of Bioactive Agent-encapsulated Vehicles

Carboxyfluorescein Encapsulated Liposomes
1,2-Dioleoyl-sn-glycero-3-Phosphoethanolamine-N-(succinyl), or succinyl PE, a commercially available phospholipid containing carboxyl groups was used for coupling to papain. The succinyl PE, 1,2-Distearoyl-sn-glycero-3-phosphochline (DSPC) and cholesterol were mixed together in a weight ratio of 1:9:3 in a chloroform solution in a warm water bath at about 60° C. A thin lipid film was subsequently formed by removing the solvent.

The carboxyfluorescein (CF) solution was added to the thin lipid film. The resulting mixture was stirred for about an hour in a water bath of about 60° C. The mixture was then pushed through a mini extruder (filter size: 0.2 μm, 20 times) and subsequently passed through a Sephadex G-25 column to separate the CF-encapsulated liposomes.

Nanoparticle-encapsulated Liposome
Poly(lactic-co-glycolic acid) (PLGA) nanoparticle-enicapsulated liposomies were prepared using a similar procedure described above except PLGA nanoparticles were used in place of CF to hydrate the lipid thin film.

Hyaluronic Acid-encapsulated Liposomes
Hyaluronic acid-encapsulated liposomes were prepared using a similar procedure described above except the fluorescein labeled hyaluronic acid with a molecular weight around 800 kDa was used to replace CF. The amount of hyaluronic acid encapsulated within the liposomes was determined by lysing the liposomes after encapsulation and measured the fluorescence intensity of the fluorescein labeled hyaluronic acid released from the liposomes.

Vitamin E and Co-enzyme Q10-encapsulated Liposome
Vitamine E and co-enzyme Q10-encapsulated liposomes were prepared using a similar procedure described above except DSPC, succinyl PE, cholesterol, vitamin E and co-enzyme Q10 were mixed in a molar ratio of 5:3:1:1:1 in a chloroforn solution. The inclusion of both vitamine E and co-enzyme Q10 within the liposomes was determined by high performance liquid chromatography (HPLC), which employed an Alltech 150×4 mm RP-18 column and a UV detector (280 nm) with a flow rate of about 0.6 ml/min.

Glucose-encapsulated Liposome
Materials 1,2-Distearoyl-sn-Glycero-3-Phosphocholine (DSPC), 1,2-Dioleoyl-sn-Glycero-3-Phosphoethanolamine-N-(succinyl) (Succinyl PE) were purchased from Avanti Polar Lipids (Alabaster, Ala.). Glucose assay kits were purchased from BioVision (Mountain View, Calif.). All other chemicals were purchased from Sigma Chemical Co. (St. Louis, Mo.). Franiz cells were purchased from PerneGeari. Inc. (Helleiltowni, Pa.).

Methods. Liposomes were prepared by a film hydration method. Briefly, the lipid compounds DSPC, succinyl PE and cholesterol in the molar ratio of 1.0:0.1:0.7 were mixed in the chloroform, and the solvent was removed by rotary evaporation to form a lipid film on the inner wall of a round bottom flask. The lipid film was further dried to remove residual organic solvent under vacuum overnight. One ml of 100 mM glucose was added to hydrate 20 mg of lipid film and the lipid suspension was maintained at 60° C. for 1 hr. After hydration, the suspension of liposomes was sonicated for 10 min. A mini extruder (Avanti Polar Lipids) was used to size the liposonie by extruding through a polycarbonate filter (0.2 μm) for 20 times at 60° C. Any un-encapsulated glucose was removed from the liposomes by gel filtration with sephadex G-25 column (GE Healthcare Bio-Sciences AB).

Example 2

Preparation of Proteolytic Enzyme-tagged Drug Vehicle

Conjugation of Papain on the Surface of Liposome
The conjugation of the primary amine group of papain compound (1 mg) with the carboxyl group of liposome ($2 \times 10^{12}$ liposome/ml) was achieved by using the coupling agent 1-ethyl-3-[3-dimethylaminopropyl]carbodiimide hydrochloride (EDC; Sigma Chemical Co) (0.2M). The coupling reaction 110 was performed in phosphate buffer saline at room temperature for 2 hr. The papain-tagged liposomes were purified by HPLC (high pressure liquid chromatography) using a size-excitision chromatographic column (Bio-Sep SEC-S2000, Phenomenex) to remove un-reacted papain.

FIG. 1 is a schematic drawing showing the coupling of papain molecules 104 to carboxyl groups 106 on the surface of the lipid bilayer of liposome 108 via the EDC coupling reaction 110. The EDC is a carboxyl and amine-reactive zero-length cross linker. The EDC reacts with the carboxyl groups 106 first and forms an amine reactive O-acylisourea intermediate that rapidly reacts with the amino group to form an amide bond. The EDC is used here to link the amine group of papain 104 to the carboxyl group 106 on liposomal surface.

Figure 2:
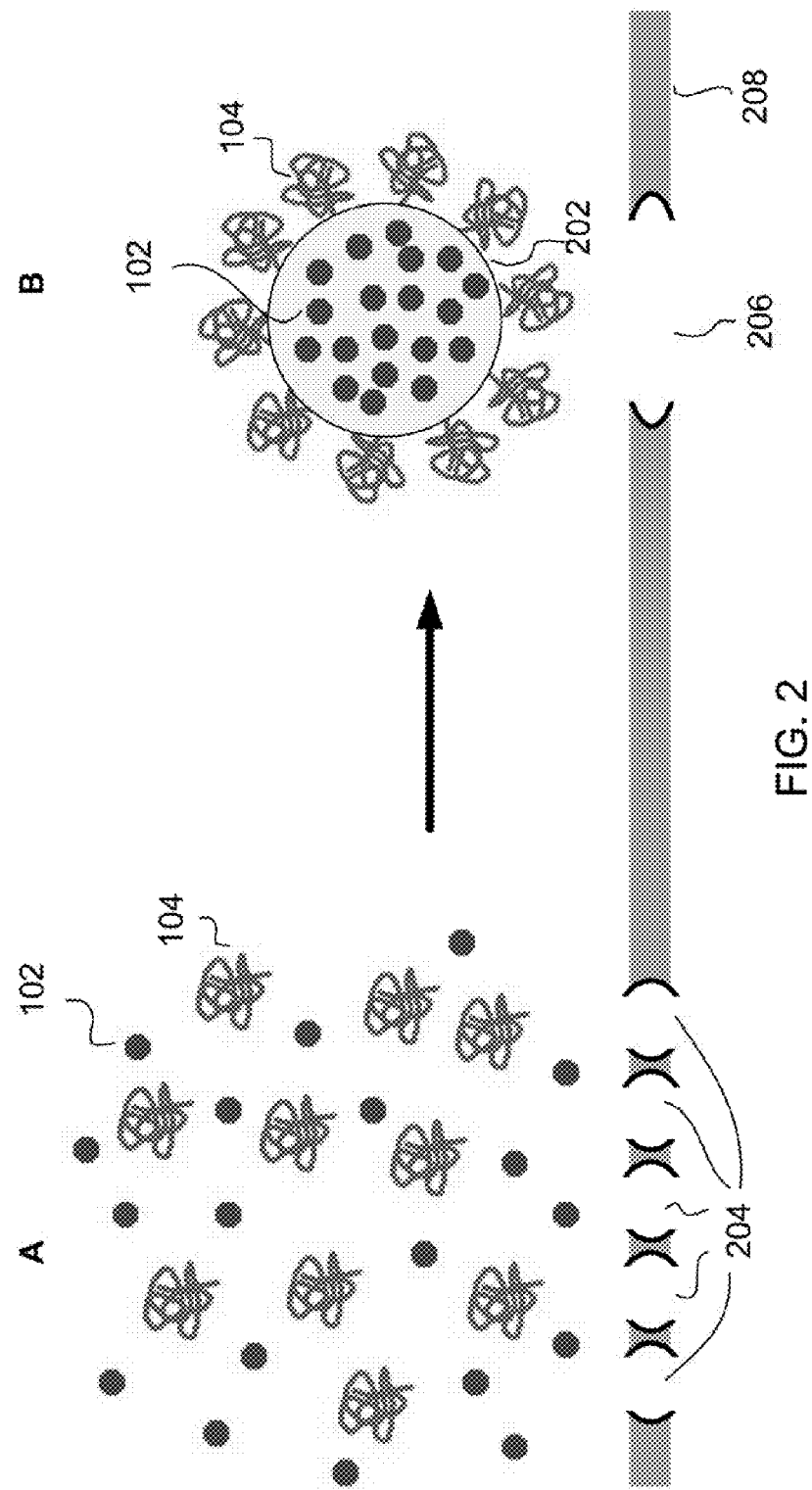
FIG. 2A is a schematic drawing of transdermal delivery of bioactive molecules 102 via proteolytic enzyme such as papain in a free form 104 as a penetration enhancer.
FIG. 2B is a schematic drawing of transdermal delivery of the bioactive molecules 102 being packaged (as indicated by the arrow) into a liposome having the proteolytic enzyme 104 of FIG. 2A attached onto the surface.

Papain 104 was considered to be a permeability enhancer for increasing transdermal permeation of certain drug molecules 102 through the skin pores 204 (FIG. 2A). Papain 104 itself is too large to permeate the viable epidermis 208. It however has posed concerns related to instability and safe concentration issues. FIG. 2B illustrates the inventive concept of utilizing a micro-sized or nano-sized drug vehicle 202 (e.g., a liposome) to concentrate bioactive molecules 102 within the vehicle and papain 104 on the surface thereof to enhance and prolong the transport of the drug molecules 102 through pores 206 of the skin 208. It was hypothesized that by concentrating papain 104 and bioactive molecules 102, the transdermal delivery efficiency would be enhanced and the total amount and the concentration of papain needed in the solution could be decreased. The skin irritation and other side effects caused by papain would thus be decreased or eliminated.

Quantification of Papain

A thiol protease chromogenic substrate, such as pGlu-Phe-Leu-p-Nitroaniliede, was used to quantify the amount of papain. Twenty microliters of 4 mM substrate dissolved in dimethyl sulfoxide (DMSO) was mixed with 165 µl of 0.1 M phosphate buffer solution (PBS, pH6.5). The mixture was incubated at 37° C. for 5 min. Papain or papain-tagged liposome solution (15 µl) (papain concentrations rangier from 0.25 mg/ml to 2 mg/ml) was added and the incubation continued at 37° C. for 20 min. The reaction was stopped by the addition of 15 µl of 3N hydrochloric acid. The absorbance of sample was recorded at 410 nm. The papain concentration of the sample solution was fitted by a standard curve of free papain. To avoid the interference from liposomes, all sample solutions were filtered by a 0.1 µm filter (Millipore) before the absorbance measurement. The total papain concentration in each test tube containing papain-conjugated liposomes was measured by the quantification method mentioned above.

Calculation of the Number of Papain Molecules Conjugated onto One Single Liposome The number of papain molecules conjugated to a single liposome (1) was calculated by dividing the total number of papain molecules ($N_{papain}$) by the total number of liposomes ($N_{liposome}$):

$$I = N_{papain} / N_{liposome}.$$

The term $N_{papain}$ represents the total number of papain molecules measured with a chromogenic substrate. The term $N_{liposome}$ represents the total number of liposomes, which was calculated by dividing the total number of phospholipid molecules by the number of phospholipid molecules in a single, 200 nm liposome (about $1.6 \times 10^5$ phospholipid molecules/liposome). The concentration of phospholipid was measured using a colorimetric method as follows: A stock solution of ammonium ferrothiocyanate was made by dissolving 27.03 g of ferric chloride hexahydrate ($FeCl_3 6H_2O$) and 30.4 g of ammonium thiocyanate ($NH_4SCN$) in 1L of deionized water. A standard calibration curve of phosphiolipid concentration was generated. Each phospholipid sample was vigorously mixed with an equal volume of salt solution for one minute. The organic phase was separated from the aqueous phase and the absorbance was recorded by UV/Vis to fit the phospholipid concentration of samples.

Calculation of Effective Papain Concentration per Single Conjugated Liposome

Figure 3:
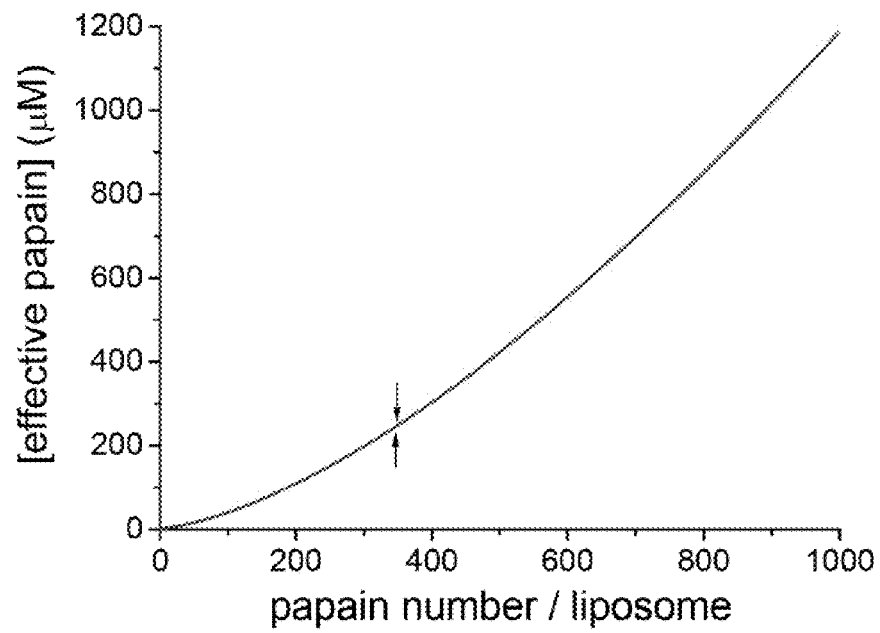
FIG. 3 shows that the effective papain concentration of each liposome is proportional to the numbers of papain molecules attached thereto.
Figure 4:
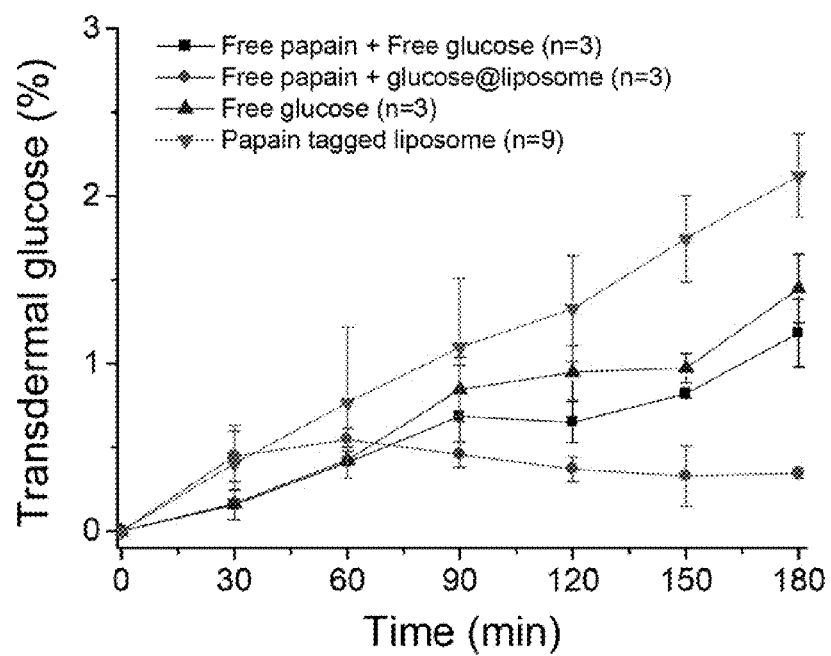
FIG. 4 shows the time course of transdermal efficiency of glucose delivered with or without free or liposome-conjugated papain.

For every enzyme-conjugated liposome, its corresponding effective enzyme concentration was calculated as follows: the total surface area of one single liposome ($A = 4 \pi R^2$) was calculated. Assuming the distribution of papain on liposome surface is homogeneous, the distance between two papain molecules was equal to $d = n^{1/2}/A^{1/2}$. The term "n" represents the papain number per liposome and the term "A" refers to the surface area of a liposoine. The volume occupied by one papain molecule is $d^3$. The calculated effective papain concentration was equal to the total mole number of papain per liter. As shown in FIG. 3, the effective papain concentration per liposome is proportional to the number of papain molecules attached.

Taking the X axis value at 350 papain molecules/liposome as an example, the corresponding effective papain concentration was 245 µM. The total papain concentration in the test tube containing papain-conjugated liposomes at 350 papain molecules/liposome was 1.18 µM. The effective papain concentration per liposme was therefore essentially increased to 208 fold (245/1.18=208) due to the fact that papain molecules were concentrated onto the surface of the liposome.

Example 3

Transdermal Delivery of Encapsulated bioactive Agent

The efficiency of the transdermal penetration of proteolytic enzyme-tagged drug vehicles was evaluated using in vitro Franz Diffusion cells. Briefly, a piece of porcine abdominal skin tissue sliced to 500 µm thickness using electric dermatome (Zimmer Inc., USA) was mounted between two half-cells of a vertical Franz Diffusion cell (R=15 mm, skin area: 1.77 $cm^2$, the volume of receiver: 12 ml) and fastened with a clamp.

The permeation efficiencies were measured on various modes of transdemial drug delivery. The following four different modes of drug delivery were tested: (1) glucose-encapsulated liposome with surface-tagged papain (350 papain/200 nm liposome, total papain 26 µg/ml, total glucose 5 mM); (2) free papain (500 µg/ml)+free glucose(5 mM) (3) Free glucose (5 mM); and (4) Free papain (500 µg/ml)+glucose-encapsulated liposome (5 mM).

Samples (1 ml per sample) from each group were applied to the donor compartment. The receiver compartment was filled with 0.1M PBS. Samples were taken every 30 minutes for 3 hrs and assayed with a glucose assay kit (BioVision Co) according to the manufacturer's instructions (TECAN, Infinite M200). All experiments were performed at room temperature.

The calculated amount of papain per tagged liposome was 0.025 mg/ml, equivalent to 350 papain molecules/liposome or equivalent to an effective papain concentration of 5.6 mg/ml. The safe concentration of papain was reported to be around 0.093 mg/ml, which is equivalent to 4 µM in solution (US005534260A).

TABLE 1*

| | Permeability (cm/hr) t (hr) | | | | | |
|---|---|---|---|---|---|---|
| | 0.5 | 1.0 | 1.5 | 2.0 | 2.5 | 3.0 |
| Papain-conjugated liposome@glucose** | 0.45 ± 0.42 | 0.43 ± 0.28 | 0.41 ± 0.20 | 0.38 ± 0.14 | 0.39 ± 0.11 | 0.40 ± 0.10 |
| Free papain + glucose*** | 0.22 ± 0.09 | 0.28 ± 0.06 | 0.30 ± 0.09 | 0.26 ± 0.08 | 0.27 ± 0.11 | 0.26 ± 0.05 |
| Enhancement | N.S. | N.S. | N.S. | N.S. | 1.40 | 1.54 |

N.S. stands for non-significant
*Total glucose is 5 mM in each sample.
**The total papain concentration in the papain-liposome@glucose solution is 25 µg/ml. The symbol "@" stands for "encapsulating."
***The concentration of free papain is 500 µg/ml.

The transdermal efficiency of glucose was compared among different delivery modes. The glucose permeability (mg/hr) was obtained under the following various conditions: (1) glucose encapsulated within papain-conjugated liposome; (2) glucose delivered by free papain alone (20-fold concentration mix with glucose) (Table 1); and (3) glucose encapsulated within liposome and delivered by free papain (Table 2). The permeability (P) is calculated by P=J/Cv, where "J" represents the amount (mg) of glucose flux through skin barrier per unit area per hour (mg/cm$^2$×hr), and "Cv" represents the concentration of bioactive molecules (mg/cm$^3$).

The results suggested that when bioactive molecules were packaged into papain-conjugated liposome, the transdermal delivery efficiency of the molecules was enhanced significantly compared to those delivered by free papain (500 µg/ml) alone. The enhanced transdermal delivery by the papain-conjugated liposome dosage form was observed despite the fact that the total concentration of papain in the papain-tagged liposoine solution was only 1/20$^{th}$ of that of the free soluble papain, i.e., 25µg/ml. The results showed that the transdermal delivery efficiency of the liposome-conjugated papain was 20-fold higher than the unconjugated.

TABLE 2*

| | Permeability (cm/hr) t (hr) | | | | | |
|---|---|---|---|---|---|---|
| | 0.5 | 1.0 | 1.5 | 2.0 | 2.5 | 3.0 |
| Papain-conjugated liposome@glucose** | 0.45 ± 0.42 | 0.43 ± 0.28 | 0.41 ± 0.20 | 0.38 ± 0.14 | 0.39 ± 0.11 | 0.40 ± 0.10 |
| Free papain + liposome@glucose*** | 0.66 ± 0.27 | 0.40 ± 0.16 | 0.28 ± 0.15 | 0.22 ± 0.53 | 0.17 ± 0.13 | 0.13 ± 0.09 |
| Enhancement | N.S. | N.S. | N.S. | 1.73 | 2.29 | 3.08 |

N.S. stands for non-significant
*Total glucose is 5 mM in each sample.
**The total papain concentration in the papain-liposome@glucose solution is 25 µg/ml. The symbol "@" stands for "encapsulating."
***The concentration of free papain is 500 µg/ml.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for enhancing delivery of a bioactive agent across a skin tissue comprising the step of:
    applying an effective amount of a composition comprising:
        a) a liposome;
        b) a bioactive agent encapsulated within the liposome;
        c) a plurality of proteolytic enzyme molecules conjugated onto the surface of the liposome; and
        d) a pharmaceutically acceptable carrier,
    for a period of time effective to deliver the bioactive agent across the skin tissue at a desired dosage.

2. The method of claim 1, wherein the composition further comprises a nanoparticle enclosed in the liposome, wherein the bioactive agent is encapsulated within the nanoparticle within the liposome.

3. The method of claim 2, wherein the nanoparticle is formed from poly(lactic-co-glycolic acid) (PLGA) or hydrogel.

4. The method of claim 1, wherein the proteolytic enzyme is papain.

5. The method of claim 4, wherein the concentration of papain is less than 93, or less than 50, 40 or 30 μg/ml.

6. The method of claim 1, wherein the proteolytic enzyme is a selected from the group consisting of papain, pancreatin, ficin, bromelain, elastase, pepsin, hyaluronidase, streptokinase, streptodornase, trypsin, chymotrypsin, α-chymotrypsin, α-amylase, deoxyribonuclease, collagenase, sutilain and any combination thereof.

7. The method of claim 1, wherein the bioactive agent comprises two or more than two types of bioactive agents.

8. The method of claim 7, wherein the two or more than two types of bioactive agents comprises at least one type of hydrophilic bioactive agent.

9. The method of claim 1, wherein the bioactive agent is a hormone.

10. A composition for transdermal administration of a bioactive agent comprising:
    a) a liposome;
    b) a bioactive agent encapsulated within the liposome;
    c) a plurality of proteolytic enzyme molecules conjugated onto the surface of the liposome; and
    d) a pharmaceutically acceptable carrier,
    wherein the proteolytic enzyme is selected from the group consisting of papain, pancreatin, ficin, bromelain, elastase, pepsin, hyaluronidase, streptokinase, streptodornase, trypsin, chymotrypsin, α-chymotrypsin, α-amylase, deoxyribonuclease, collagenase, sutilain and any combination thereof.

11. The composition of claim 10, wherein the enzyme is papain.

12. The composition of claim 11, wherein the concentration of papain is less than 93, or less than 50, 40 or 30 μg/ml.

13. The composition of claim 10, wherein the composition further comprises a nanoparticle enclosed within the liposome, and wherein the bioactive agent is encapsulated within the nanoparticle within the liposome.

14. The composition of claim 13, wherein the nanoparticle is formed from poly(lactic-co-glycolic acid) (PLGA) nanoparticle or hydro-gel.

15. A composition for transdermal administration of a bioactive agent comprising:
    a) a liposome;
    b) a bioactive agent encapsulated within the liposome;
    c) a plurality of papain molecules conjugated onto the surface of the liposome; and
    d) a pharmaceutically acceptable carrier.

16. The composition of claim 15, wherein the concentration of papain is less than 93, or less than 50, 40 or 30 μg/ml.

17. The composition of claim 15, wherein the composition further comprises a nanoparticle enclosed within the liposome, and wherein the bioactive agent is encapsulated within the nanoparticle within the liposome.

18. The composition of claim 17, wherein the nanoparticle is formed from poly(lactic-co-glycolic acid) (PLGA) nanoparticle or hydro-gel.

19. The method of claim 15, wherein the bioactive agent comprises two or more than two types of bioactive agents.

* * * * *